United States Patent [19]

Heng et al.

[11] Patent Number: 5,470,709
[45] Date of Patent: Nov. 28, 1995

[54] GENE MAPPING BY HYBRIDISATION TO FREE CHROMATIN

[75] Inventors: Henry H. Q. Heng, Toronto; Lap-Chee Tsui, Etobicoke, both of Canada

[73] Assignee: HSC Research & Development Ltd. Partnership, Toronto, Canada

[21] Appl. No.: 122,141

[22] Filed: Sep. 16, 1993

[30] Foreign Application Priority Data

Sep. 16, 1992 [CA] Canada .................................. 2078377-0

[51] Int. Cl.[6] .................................................. C12Q 1/68
[52] U.S. Cl. ................................. 435/6; 935/77; 935/78
[58] Field of Search ..................................... 435/6; 436/94

[56] References Cited

PUBLICATIONS

Parra et al. (Sep. 1993) Nature Genetics, vol. 5, 17–21.
Freifelder, David, Molecular Biology, Second Ed., Jones and Bartlett Publishers, Inc. Boston (1987) p. 105.
Heng et al., High–Resolution mapping of mammalianenes by in situ hybridization to free chromatin (Oct. 1992) PNAS (89) pp. 9509–9513.
Lichter et al., "*High–Resolution Mapping of Human Chromosome 11 by in Situ Hybridization with Cosmid Clones*", Science 247:64–69 (1990).
Yao—Shan Fan et al., "*Mapping small DNA sequences by fluorescence in situ hybridization directly on banded metaphase chromosomes*", Genetics 87:6223–6227 (1990).
Lawrence et al., "*Interphase and Metaphase Resolution of Different Distances Within the Human Dystrophin Gene*", Science 249:928–932 (1990).
Trask et al., "*The Proximity of DNA Sequences in Interphase Cell Nuclei is Correlated to Genomic Distance and Permits Ordering of Cosmids Spanning 250 Kilobase Pairs*", Genomics 5:710–717 (1989).
Ferguson—Smith, "*Invited Editorial: Putting the Genetics Back Into Cytogenetics*", Am. J. Jum. Genet 48:179–182 (1991).
Trask, "*Fluorescence in situ hybridization: applications in cytogenetics and gene mapping*", Trends in Genetics 7:149–154 (1991).
Brandriff et al., "*A New System for High–Resolution DNA Sequence Mapping in Interphase Pronuclei*", Genomics 10:75–82 (1991).
Heng et al., "*Studies on the Structure of the Chromosome and its Formation*", The Nucleus 29:5–8 (1986).
Heng et al., "*Effects of pingyanymycin on chromosomes: A possible structural basis for chromosome aberration* ", Mutation Research 199:199–205 (1988).
Heng et al., "*The Study of the Chromatin and the Chromosome Structure for Bufo Gargarizans by the Light Microscope*", J. Sichuan Univ. Natural Science 2:105–108 (1985).

*Primary Examiner*—Margaret Parr
*Assistant Examiner*—Lisa Arthur
*Attorney, Agent, or Firm*—Bell, Seltzer, Park & Gibson

[57] ABSTRACT

A method is provided for detecting, ordering and mapping genes or DNA sequences in the genome of eukaryotic cells. The method comprises the steps of releasing free chromatin from the nuclei of the cells and contacting the released free chromatin with at least one detectable probe capable of hybridizing to the genes or DNA sequences to be detected, thereby rendering the genes or DNA sequences detectable.

20 Claims, 4 Drawing Sheets

GENE MAPPING BY HYBRIDISATION TO FREE CHROMATIN

BACKGROUND OF THE INVENTION

Determination of the physical locations of genes and DNA segments on individual chromosomes is an important aspect of genome research. Correct orientation and ordering of these markers are also crucial in identification of disease genes on the basis of chromosome location. Besides crude mapping methods, such as the use of interspecific somatic cell hybrids containing various subsets or portions of human chromosomes, isotope-labelled probe hybridization to genomic DNA in metaphase chromosomes presents a direct approach to localization of genes to specific chromosomal regions with high precision. In combination with fluorescence-labelling, the resolving power of in situ hybridization has been greatly improved; it is also possible to assign relative positions of genes and DNA segments as close as 1–2 megabase (Mb) apart.

More recently, the introduction of fluorescence in situ hybridization (FISH) with less-condensed chromatin of interphase nuclei or pronuclei further increases the resolution, to around 50–100kb. A major limitation of FISH mapping with interphase nuclei, however, is that the chromatin fibers are organized three-dimensionally, so that gene order can only be inferred by estimating the maximal distance between two probes. Interphase FISH mapping becomes less accurate as the distances between probes increases and the interpretation is complex for multiple fluorescent-conjugate data. On the other hand, although methods such as pulsed field gel electrophoresis and cloning with yeast artificial chromosomes often permit accurate short-range ordering of specific genomic regions, these techniques will have limited applications for the entire genome until sufficient evenly spaced probes are available.

SUMMARY OF THE INVENTION

A method is provided for detecting, ordering and mapping genes or DNA sequences in the genome of eukaryotic cells comprising:

(a) treating the cells to release free chromatin from the nuclei of the cells;

(b) contacting the released free chromatin with at least one detectable probe capable of hybridizing to the genes or DNA sequences to be detected, thereby rendering the genes or DNA sequences detectable.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Certain embodiments of the invention are described, reference being made to the accompanying drawings, wherein:

FIG. 5: Correlation between the expected and observed physical distances in free chromatin mapping. Each measurement was performed 10–50 times with hybridization signals derived from slides of the same preparation; the average distance was shown with standard deviation.

DETAILED DESCRIPTION OF THE INVENTION

Figure 1A:
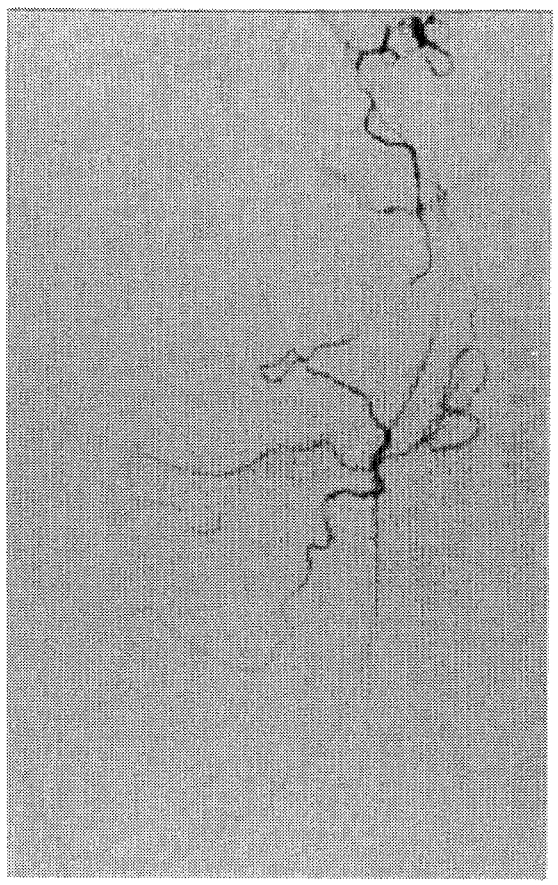
FIG. 1A, B Detection of free chromatin structures by DNA binding dyes (1000×). (a) elongated free chromatins stained with Giemsa. (b) Two interphase nuclei and two spindle like free chromatin after staining with DAPI. The procedures were the same as described in Table 1.
Figure 1B:
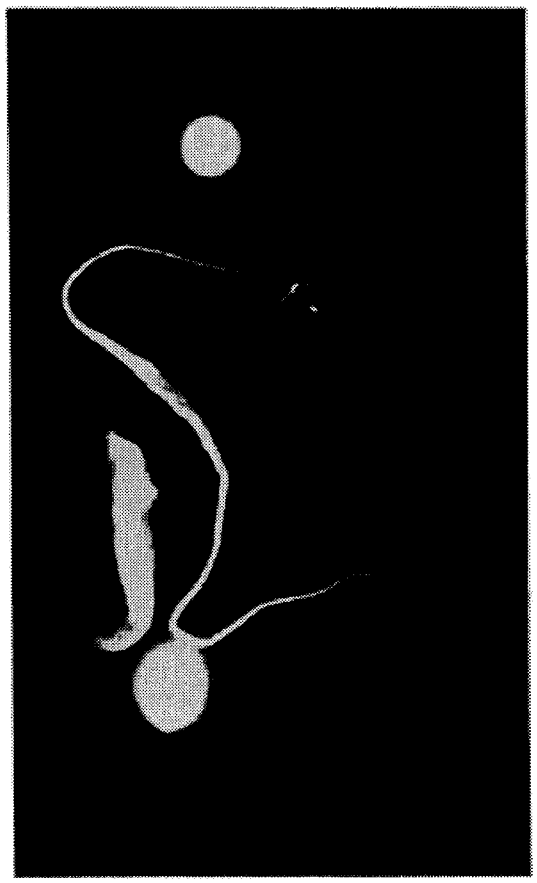

In routine examination of human metaphase chromosome preparations by light microscopy, different chromatin structures can sometimes be identified. In addition to the typical condensed mitotic chromosomes and spherical interphase nuclei containing uncondensed chromatin fibers, several other more elongated structures may be detected (FIG. 1). Some of these structures have a spindle shape with tapered ends and some have long dispersed rope-like ends well separated from one another. It has been shown that these structures are chromatin fibers released from nuclei and that they can be readily stained with DNA-specific dyes such as Feulgen and 4,6-diamidino-2,3-phenyl-indole dihydrochloride (DAPI). The term "free chromatin" has thus been used to describe these released chromatin fibers.

It was not suspected that "free chromatin" could be maintained in such structural integrity that it could be useful for gene mapping.

The present inventors have found unexpectedly that gene mapping may be carried out using free chromatins released from interphase nuclei of mammalian or other eukaryotic cells. The present invention provides convenient, rapid and simple methods for releasing free chromatin suitable for gene mapping from interphase nuclei with high resolution and high end coverage.

In accordance with the invention, single-copy DNA sequences in free chromatin can be specifically detected by FISH without the use of sophisticated imaging. The resolution of this technique is estimated to be around 10–20 kb and it should be broadly useful for physical mapping and ordering of genes in mammalian or other complex genomes.

Other in situ hybridization techniques besides FISH may be applied to free chromatin and will be known to those skilled in the art.

EXAMPLES

Certain embodiments of the invention are described in the following non-limiting examples.

Example 1

Lymphocytes isolated from healthy donors or human cord blood were cultured in α-minimal essential medium (MEM) supplemented with 10% fetal calf serum and phytohemagglutinin, in a $CO_2$ incubator at 37° for 48–52 hr.

Cultures were either maintained as controls or treated with various concentrations of N-methanesulfonamide (m-AMSA, gift of the Drug Synthesis Branch, National Cancer Institute, USA) for 2 hr.

The cells were collected and subjected to a standard hypotonic treatment used for study of metaphase chromosomes, KCl (0.4%) for 10 min at 37° C., and rinsed twice with 3:1 methanol:acetic acid. The cell suspension was dropped on ice-cold slides and air-dried for subsequent cytogenetic and hybridization analyses. Slides can be stored at −20° C. for at least 6 months before use for hybridization analyses. The proportion of free chromatin in each preparation was examined after staining sample slides with 3% Giemsa solution (pH 6.8, Fisher Diagnostics) for 10 min.

m-AMSA may be replaced by other drugs which inhibit chromosome condensation, including the pingyanymycin family of drugs. Other suitable drugs will be known to those skilled in the art and include 5-Bromo-2'-deoxyuridine (Brdu), Ethidium bromide (EB) and Hoechst 33458 (H-33258).

It will be understood by one skilled in the art to screen several drug concentrations for treating the cells and to select the one giving the most satisfactory free chromatin preparations by examination after Giemsa staining as described above. It is desirable that around 1 to 5% of the cell population shows elongated free chromatin.

As expected, the proportion of extended chromatin structures in a conventional metaphase preparation from peripheral blood culture was generally low. Typical free chromatins were operationally defined as bundles of fibrous structures at least 5 times longer than the mean diameter of the nuclei. Based on the analysis of over 100 individuals, the average frequency of such structures among the interphase nuclei and mitotic figures was around 0.3% and there appeared to be significant variation in the proportion of these structures among samples from different individuals. The proportion of free chromatin structures, however could be increased with a variety of reagents and culture conditions; for example, the anti-neoplastic drug pingyanymycin was effective in inducing free chromatin from lymphocyte preparations.

Where m-AMSA was used, as much as 2.1% of the structures were found to be typical free chromatins (Table 1). Fifteen percent of these structures reached 200–300 μm in length. Typical free chromatin preparations by the method of Example 1 are shown in FIG. 1.

TABLE I

Dose-responsive induction of free chromatin structures from human lymphocytes (of a single donor) with m-AMSA.

| m-AMSA conc. (ug/ml) | Number of structures examined | percent of free chromatin | percent of mitotic figures | percent of interphase nuclei |
|---|---|---|---|---|
| None | 10,129 | 0.24 | 4.2 | 95.6 |
| 0.5 | 10,299 | 0.28 | 1.5 | 98.2 |
| 1.0 | 9,285 | 0.69 | 1.1 | 98.2 |
| 5.0 | 9,494 | 0.72 | 0.4 | 98.3 |
| 10 | 9,830 | 2.1 | 0.4 | 97.5 |
| 20 | 9,846 | 1.6 | 0.4 | 98.0 |
| 40 | 9,814 | 1.6 | 0.3 | 98.2 |

It was found that if lymphocytes were cultured for more than about 48–52 hrs., the amount of free chromatin released by hypotonic treatment dropped. Lymphocytes were therefore not cultured for more than 48–52 hrs.

Fibroblastoid cells were found not to respond very well to this technique and were better treated with alkaline buffer, as described in Example 2.

Example 2

Lymphocytes from healthy donors or human cord blood were cultured for about 48–52 hours in medium as in Example 1. Cultures were treated with thymidine (0.3 mg/ml) for 20 hr. The synchronized cultures were then washed three times with serum free medium to release the thymidine-block and incubated for ~10 hr in α-MEM to enrich for free-chromatins from the G1 phase.

Cells were then harvested and resuspended in a borate buffer (1 mM sodium borate adjusted to a pH in the range of about 10.0–11.5 with NaOH and containing 0.2–2% KCl) at room temperature for 2–10 min. to break open the nuclear envelope and release free chromatin.

Since the degree of free chromatin release in response to these conditions varied somewhat from batch to batch of cells, the time of incubation, pH and KCl concentration were adjusted to give optimal free chromatin release, which was assessed as described in Example 1.

The proportion of free chromatin released was greatly increased by this high pH buffer treatment particularly for fibroblastoid cell lines, for which this treatment gave superior results to m-AMSA treatment.

Thymidine treatment may be omitted but is preferred in order to accumulate cells in the G1 phase.

For cells which grow in contact with a surface, these were allowed to grow to confluence and once G1 phase was reached, the cells were harvested by conventional methods.

The method gave excellent free chromatin release with a variety of different cell types, including CHO, Hela, human/mouse hybrid cell lines and human/hamster hybrid cell lines.

As will be known to these skilled in the art, other suitable buffers capable of maintaining the described pH range may be substituted for borate buffer.

If alkaline buffer solution alone is used to break open the nuclear envelope, there is a tendency for too much free chromatin to be released very quickly, giving overlapping DNA strands and tangles which are not well suited to gene mapping.

Addition of a salt to the alkaline buffer, at a concentration in the range of about 0.2% to about 4.0% by weight, results in a more gradual release of free chromatin, giving satisfactory preparations for gene mapping and other studies. Suitable salts will be known to those skilled in the art or can be determined by examining the degree of chromatin release as described in Example 1.

Especially preferred is KCl at a concentration of about 0.2 to about 2%.

Other substances also may be used as agents to moderate the rate of chromatin release by alkaline buffer; for example sucrose at a concentration of about 0.2% to about 10% by weight may be used instead of salt. Other suitable substances can be determined by those skilled in the art.

Example 3

For certain cell types, it has been found sufficient for good release of free chromatin to accumulate cells in the phases immediately prior to or immediately after metaphase and to subject these cells to hypotonic treatment.

Cultured cord blood lymphocytes were treated by thymidine block, followed by release, as described in Example 2.

Cells were then harvested around 10 hours after release from thymidine block and subjected to standard hypotonic treatment as described in Example 1, giving satisfactory release of free chromatin for gene mapping.

Example 4

For certain populations of cells, it has been found that there may be a sufficient proportion of cells which can release free chromatin for gene mapping studies by standard hypotonic treatment alone. For example, lymphocytes obtained from human cord blood may be prepared for gene mapping by this technique without culture.

Lymphocytes were collected and treated with 0.4% KCl as described in Example 1 and slides were prepared for free chromatin studies as described in that example.

Example 5

Use of free chromatin for gene mapping cosmids and somatic cells. The cosmid clones cM58-3.6, CF14, cJ21 and cW10–20 were derived from the 7q31 region as previously described. Four of these cosmids were mapped upstream of the cystic fibrosis transmembrane conductance regulator (CFTR) gene whereas cosmid cW10–20 was found to contain exons 4, 5, 6a, 6b and 7 of the gene. The human hamster somatic hybrid cell line 4AF/102 contained a single human chromosome 7 as its only human material; the other cell hybrid, ATCC number GM10323, was specific for human chromosome 21.

Microscopy and distance analysis. The photographs were taken with a Nikon Microphot-FXA epifluorescence microscope equipped with dual band FITC/Texas red filters (Omega Optical Inc.). Kodak color Ektachrome P800/1600 "push level 2" E-6P professional film was used with typical exposure times of 30–90 sec. The distance measurements were obtained from projected images of photographic slides.

Fluorescence in situ hybridization. FISH was performed according to published procedures. Briefly, the slides were aged for 20–30 days prior to denaturation by 70% formamide in 2xSSC at 70° C. for 3 min and followed by dehydration in ethanol. Total human DNA or cosmid probes were prepared according to standard procedures. Probes were labelled with biotinylated dATP (the BRL BioNick Labelling system). Approximately 20 ng of the biotinylated probe were added to each slide together with 10 μg of salmon sperm DNA in 12 μl of hybridization buffer (50% formamide, 1xSSC and 10% dextran sulphate).

For total human DNA probe, hybridization was performed for 16–20 hr at 37° C. Post-hybridization washing consisted of three 5-min immersions in 50% formamide and 2xSSC, followed by 2xSSC and 0.1xSCC at 42° C. The slides were then immersed in a solution containing 3% BSA and 4xSSC for 30 min prior to incubating in 5 μg/ml fluorescein isothiocyanate (FITC) conjugated to avidine (Vector laboratories) in 1% BSA, 0.1% Tween 20 and 4xSSC. Unbound fluorophores were removed by three 3-min rinses in the same solution without FITC and the slides were counterstained with 40 μg/ml DAPI. After a final washing in PBS for 5 min, the slides were mounted in 90% glycerol with 20 mM Tris-HCl(pH 8) and 2.3% of DAPCO antifade (1,4-diazabicyclo-octane).

The procedure for cosmid probes was similar to that described above, except the slide baking (60°–65° C., 103 hr) and inclusion of RNase treatment (60 min at 370 with 100 82 g/ml RNase A in 2xSSC), repetitive sequence suppression (15–30 min prehybridization at 37° with 2 μg/ml sonicated total human DNA) and signal amplification (with biotinylated goat antiavidine antibody and FITC-avidine, Vector Lab.).

To demonstrate the use of free chromatin for gene mapping, in accordance with one embodiment of the invention, the inventors examined the hybridization pattern of human DNA in human/rodent somatic cell hybrid lines using FISH with a biotinlabelled total human DNA probe.

Free chromatin preparations were made by the method of Example 2.

Figure 2A:
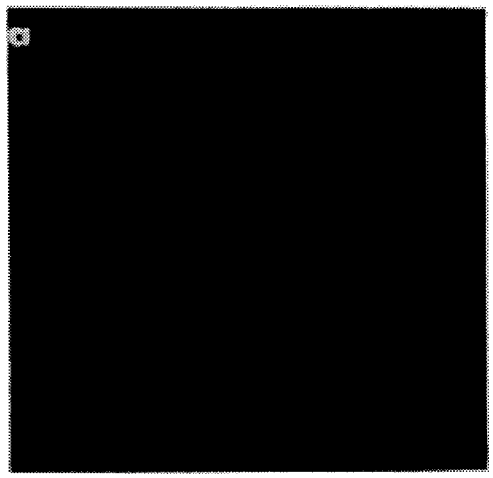
FIG. 2A, B, C, D: Visualization of free chromatin by the FISH technique (1000×). (a) The chromosome 7-specific somatic hybrid cell line 4AF/102 metaphase spread stained with DAPI to show the hamster and human chromosomes; (b) DAPI-staining of free chromatin from the same cell line to shown the total hamster and human DNA content; (c) The same metaphase preparation as in (a) with FISH detection showing hybridization of human chromosome 7; (d) Human chromosome 7 was visualized as a long fiber in the free chromatin after FISH and fluorescein isothiocyanate (FITC) detection.
Figure 2C:
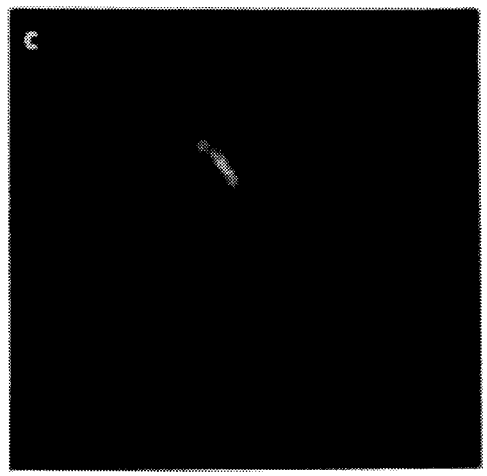
Figure 2B:
Figure 2D:

In the control experiment (FIG. 2a, c), a bright hybridization signal could be readily identified for the single metaphase chromosome 7 in a background of hamster chromosomes in the cell line 4AF/102, demonstrating the specificity of the probe. The hybridization pattern with free chromatin structures released from cell cultures at the G1 phase was then examined. As shown in FIG. 2d, a long, thin, and somewhat discontinuous hybridization signal could be detected among each of the fibrous free chromatin bundles.

In another experiment biotin-labelled total human DNA probe was incubated with free chromatin preparations from a somatic cell hybrid line containing chromosome 21 as its only human chromosomal material as well as from 4AF/102. Again, elongated thread-like hybridization signals were detected in the chromosome 21-only cell line as in 4AF/102.

The above studies therefore demonstrated that free chromatin structures are greatly extended chromosomes and that they can be readily detected by FISH. The discontinuous hybridization patterns observed are probably due to the uneven distribution of repetitive DNA along human chromosomes.

Figure 3:
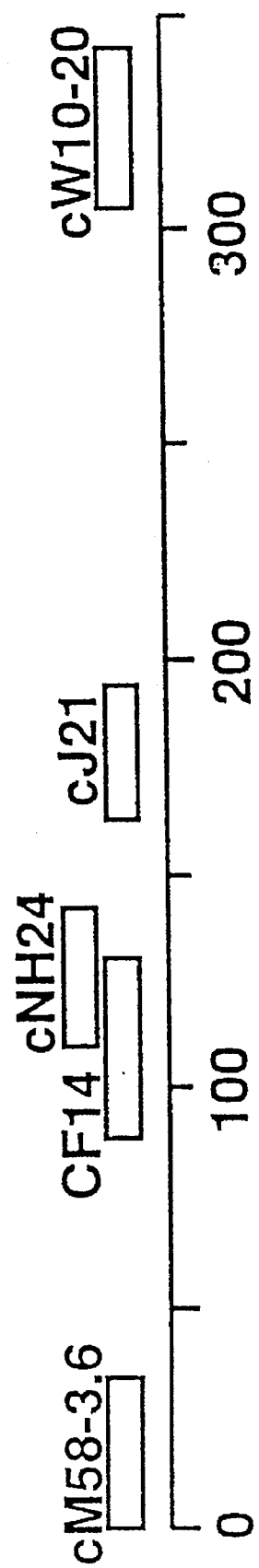
FIG. 3: Physical map of the region containing the five cosmids used in this study. The map was determined by detailed restriction mapping of cloned DNA.

The hybridization pattern was examined with a set of five cosmids in a region containing the cystic fibrosis transmembrane conductance regulator gene (7q31) for which a detailed physical map was known (FIG. 3). To avoid possible confusion of hybridization signals from the sister chromatids blocked at the G2 phase by m-AMSA, the inventors also switched to the use of cell culture at the G1 phase. Since a single human chromosome 7 was present in 4AF/104, there should be only one set of hybridization signals in the free chromatin prepared from the G1 phase culture of this cell line.

Figure 4A:
FIG. 4A, B, C, D, E, F: Detection of single-copy sequences in metaphase chromosome, interphase nuclei and free chromatin preparations by FISH (1700×). (a) Metaphase chromosomes from human diploid lymphocyte culture were hybridized with four cosmids probes cM58-3.6, cF14, cJ21 and cW10–20 together, spanning a total distance of 341 kb (see FIG. 3). (b) Hybridization of the same probes as in (a) with G1 phase nucleus; arrows indicate two sets of signals. (c,d and f) Results of hybridization with different combinations of the cosmids to free chromatin prepared from G1 phase nuclei of cultured lymphocytes; only a section of free chromatins showing one set of hybridization signals is shown. (e) Results of hybridization to somatic hybrid cell line 4AF/102; the two sets of hybridization signals represent the two sister chromatids of chromosome 7 at the G2 phase. Probes used: (c) cNH24 and cJ21; (d) cM58-3.6 and cJ21; (e) cM58-3.6, CF14 and cJ21; (f) cM58-3.6, CF14, cJ21 and cW10–20.
Figure 4C:
Figure 4D:
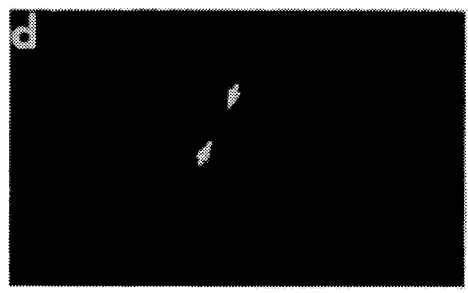
Figure 4B:
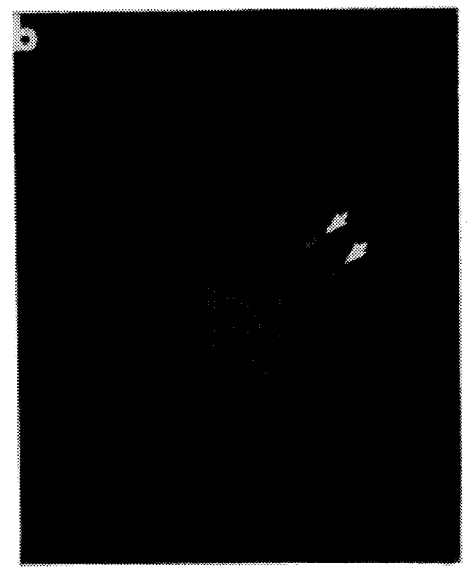
Figure 4E:
Figure 4F:
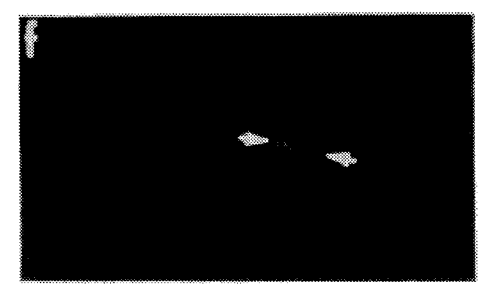

Accordingly, after testing in conventional FISH mapping with metaphase chromosomes (FIG. 4a) and interphase nuclei (FIG. 4b), these probes were used in hybridization with the free chromatin preparations, prepared as described in Example 2.

As shown in FIG. 4c–f, discrete fluorescent signals were readily detectable with cosmid probes in different combinations; two, three or four spots could be identified with the corresponding number of hybridization regions (FIG. 3), demonstrating the feasibility of this mapping technique with single-copy DNA sequences. The efficiency of hybridization with free chromatins had not been fully evaluated, but it appeared to be roughly the same as mapping with interphase nuclei (~90%).

A good correlation was also found between the distance determined from the hybridization signals and their physical map in kb (FIG. 5). For example, the intervals between the four probe-hybridizing regions (c.M58-3.6, CF14, cJ21 and cW10–20), measured from mid-point to mid-point in a pair-wise manner, was 0.9±0.3 μm, 2.14±0.48 μm and 4.0±1.1 μm, which correspond well with 63, 167 and 301 kb from fine restriction mapping (FIG. 3), respectively. Further, although the boundaries of each hybridization region could not be precisely determined, the signals were clearly discernible even for the two closest probes (cNH24 and cJ21) which were only 21 kb apart (FIG. 4c, the mean space measured between the two signals was 0.3 μm).

Using a simple alkaline releasing buffer and FISH, the inventors have developed a novel free chromatin mapping technique useful for determining gene orders in mammalian genomes. The utility of this technique compares well with all the advantages offered by mapping with the interphase nuclei or pronuclei. The added advantage of the free chromatin mapping technique is the fact that the hybridization signals are detected along the extended fibers on the same plane whereas those obtained with the interphase nuclei are distributed three-dimensionally. Thus, while it may be tricky to determine the order of multiple genes with interphase nuclei, the task can be achieved with relative ease with free chromatins. Using the present protocol, the inventors have been able to determine the order of three or more probes in a single hybridization reaction with a few (typically 1 to 3) properly-prepared slides.

The high resolution power of the free chromatin mapping technique has been demonstrated with single-colored FISH which could distinguish the signals from two DNA sequences separated by 21 kb. An excellent correspondence between the observed and expected distances has been obtained for genomic DNA sequences as far as 350 kb apart.

With the use of multicolor fluorescence conjugates, it is likely that free chromatin mapping will readily resolve gene sequences separated by as little as 10 kb. The technique will also allow simultaneous detection of signals spanning several Mb.

Therefore, free chromatin mapping represents an extremely powerful technique for genome analysis and it should complement the currently existing physical and genetic mapping strategies in any large scale efforts.

Since the free chromatin FISH mapping technique is insensitive to distribution of rare-cutting restriction enzyme recognition sites, it will be particularly useful for studying genomic DNA regions where traditional cloning and long-range restriction mapping have not been straightforward. For example, the technique may be used to define the fine structure and organization of the different types or subfamilies of repetitive elements at the centromeres and telomeres. Similarly, free chromatin FISH mapping may be applied to studies of gene amplification, translocation and deletion, where genomic DNA rearrangement is often too complex for traditional methods of analysis.

An important feature of free chromatin mapping is direct visualization of genes or DNA fragments, as well as related protein components. The concept of direct visualization of DNA probes along less condensed chromatin fibers or DNA fibers has revolutionized FISH detection.

Some speculations may be offered to explain the mechanism leading to free chromatin formation. The anti-tumour drug mAMSA used in this study is a potent inhibitor of topoisomerase II, which is thought to be required for chromosome condensation. This observation implies that m-AMSA directly interferes with chromatin condensation and arrests the chromosomes at a transient stage not normally amenable to routine cytogenetic preparation methods. On the other hand, the high pH buffer may simply destabilize the nuclear envelope, releasing chromatin fibers from the cell regardless of the stage of cell cycle. Since the use of cell cultures at the G1 phase is important for ordering genes or DNA segments, the latter technique is particularly useful when combined with a synchronized cell population.

The methods of the invention will be useful for mapping and localizing human and other mammalian genetic sequences and in detecting and localizing disease-related genes. The methods of the invention will also be useful in medical genetic diagnostic procedures, for example in situations involving translocations.

REFERENCES

1. Lichter, P. et al. Science 247, 64–69 (1990).

2. Fan, Y. S., Davis, L. M. & Show, T. B. Proc. natl. Acad. Sci. U.S.A. 87, 6223–6227 (1990).

3. Lawrence, J. B., Singer, R. H. & McNeil, J. A. Science 249, 928–932 (1990).

4. Trask, B., Pinkel, D. & van den Engh, G. Genomics 5, 710–717 (1989).

5. Ferguson-Smith, M. A. Am. J. Hum. Genet. 48:179–182 (1991).

6. Trask, B. J. Trends Genet, 7, 149–154 (1991).

7. Brandriff, B., Gordon, L. & Trask, B. Genomics 10, 75–82 (1991).

8. Heng. H. Q. & Chan, W. Y. J. Sichuan Univ. Natural Science 2, 105–108 (1985).

9. Heng, H. Q. & Chan, W. Y. The Nucleus 29, 5–8 (1986).

10. Heng, H. Q., Chan, W. Y. & Wang, Y. C. Mutation Res. 199, 199–205 (1988).

11. Arfin, S. et al. Somat. Mol. Genet. 9, 517–531 (1983).

12. Moyzis, R. K. et al. Genomics 4, 273–289 (1989).

13. Rommens, J. M. et al. Science 245, 1059–1065 (1989).

14. Adachi, Y., Luck, N. & Laemmli, U.k. Cell 64, 137–148 (1991).

15. Drlica, X. & Franco, R. Biochemistry 27, 2253–2259 (1988).

We claim:

1. A method for detecting and mapping DNA sequences from eukaryotic cells comprising:

(a) treating the cells to release free chromatin from the nuclei of the cells;

(b) contacting the released free chromatin with at least one detectable probe specific for the DNA sequences to be detected;

(c) detecting hybridization of the probe with the DNA sequences on the released free chromatin in order to detect the presence of the DNA sequences; and (d) mapping the DNA sequences.

2. The method of claim 1 wherein the released free chromatin is fixed on a suitable support prior to step (b).

3. The method of claim 2 wherein step (a) comprises contacting the cells with an alkaline solution for a time effective for release of the free chromatin.

4. The method of claim 3 wherein step (a) comprises contacting the cells with a buffer solution of pH in the range of about 10.0 to about 11.5 for 2 to 10 minutes.

5. The method of claim 4 wherein the cells are mammalian cells.

6. The method of claim 5 wherein the cells are human cells.

7. The method of claim 5 wherein the cells are selected from the group consisting of lymphocytes, fibroblastoid cells and cultured cell lines.

8. The method of claim 3 wherein, prior to step (a), the cells are cultured for about 48 hours to about 52 hours.

9. The method of claim 4 wherein, prior to step (a), the cells are cultured for about 48 to about 52 hours.

10. The method of claim 3 wherein, prior to step (a), the cells are cultured for about 48 to about 52 hours, followed by thymidine block for about 20 hours, release from thymidine block by washing and further cultured for about 10 hours.

11. The method of claim 4 wherein, prior to step (a), the cells are cultured for about 48 to about 52 hours, followed by thymidine block for about 20 hours, release from thymidine block by washing and further cultured for about 10 hours.

12. The method of claim 3 wherein the alkaline solution further comprises an agent effective to moderate the rate of free chromatin release.

13. The method of claim 12 wherein the agent is a salt or sucrose at a concentration effective for moderating the rate of chromatin release.

14. The method of claim 2 wherein, prior to step (a), the cells are cultured for about 48 to about 52 hours and then treated for about two hours with an amount of an inhibitor of chromosome condensation which is effective for inhibiting chromosome condensation.

15. The method of claim 14 wherein the inhibitor is selected from the group consisting of N-methanesulfonamide (m-AMSA), 5-bromo-2'-deoxyuridine, ethidium bromide and a pingyanymycin and wherein step (a) comprises contacting the cells with a hypotonic solution.

16. The method of claim 15 wherein the inhibitor is m-AMSA at a concentration of 5 µg/ml to 20 µg/ml, the cells are human cells, and the hypotonic solution is KCl of a concentration in the range of about 0.2% to about 2.0%.

17. The method of claim 16 wherein the cells are lymphocytes and the hypotonic solution is 0.4% KCl.

18. The method of claim 2 wherein step (a) comprises contacting the cells with a hypotonic solution.

19. The method of claim 18 wherein the cells are uncultured human lymphocytes.

20. The method of claim 19 wherein the hypotonic solution is KCl of a concentration in the range of about 0.2% to about 2.0%.

* * * * *

UNITED STATES PATENT AND TRADEMARK OFFICE
CERTIFICATE OF CORRECTION

PATENT NO.   :   5,470,709
DATED        :   November 28, 1995
INVENTOR(S)  :   Henry H. Q. Heng and Lap-Chee Tsui It is certified that error appears in the above-identified patent and that said Letters Patent is hereby corrected as shown below:

Column 6, Line 20 delete "82 g/ml" and insert --µg/ml--

Signed and Sealed this

Fourteenth Day of May, 1996

Attest:

BRUCE LEHMAN

Attesting Officer        Commissioner of Patents and Trademarks